US011821029B2

(12) United States Patent
Daum et al.

(10) Patent No.: US 11,821,029 B2
(45) Date of Patent: Nov. 21, 2023

(54) MULTIPURPOSE COMPOSITIONS FOR COLLECTING AND TRANSPORTING BIOLOGICAL MATERIAL

(71) Applicant: Longhorn Vaccines and Diagnostics, LLC, Bethesda, MD (US)

(72) Inventors: Luke T. Daum, San Antonio, TX (US); Gerald W. Fischer, Bethesda, MD (US)

(73) Assignee: Longhorn Vaccines and Diagnostics, LLC, Bethesda, MD (US)

( * ) Notice: Subject to any disclaimer, the term of this patent is extended or adjusted under 35 U.S.C. 154(b) by 68 days.

(21) Appl. No.: 17/010,410

(22) Filed: Sep. 2, 2020

(65) Prior Publication Data

US 2021/0079450 A1 Mar. 18, 2021

Related U.S. Application Data

(60) Provisional application No. 62/965,380, filed on Jan. 24, 2020, provisional application No. 62/901,342, filed on Sep. 17, 2019.

(51) Int. Cl.
*C12Q 1/686* (2018.01)
*C12Q 1/6869* (2018.01)

(52) U.S. Cl.
CPC ........... *C12Q 1/686* (2013.01); *C12Q 1/6869* (2013.01)

(58) Field of Classification Search
CPC ........ C12Q 1/686; C12Q 1/6869; C12Q 1/68; C12Q 2527/125
See application file for complete search history.

(56) References Cited

U.S. PATENT DOCUMENTS

| | | | | |
|---|---|---|---|---|
| 5,702,944 A * | 12/1997 | Racioppi | ................... | C12N 1/04 435/243 |
| 5,925,510 A | 7/1999 | Schulsinger | | |
| 8,084,443 B2 * | 12/2011 | Fischer | ................ | C12Q 1/6806 514/75 |
| 9,845,489 B2 | 12/2017 | Whintey | | |
| 2009/0081678 A1 | 3/2009 | Ryan | | |
| 2009/0312285 A1 | 12/2009 | Fischer | | |
| 2011/0165610 A1 | 7/2011 | Baker | | |
| 2014/0186821 A1 | 7/2014 | Daum | | |
| 2017/0215410 A1 | 8/2017 | Truckee | | |
| 2017/0226469 A1 | 8/2017 | Birnboim | | |

FOREIGN PATENT DOCUMENTS

| | | |
|---|---|---|
| CN | 110438089 | 11/2019 |
| WO | WO 1999/299410 | 6/1999 |

OTHER PUBLICATIONS

Botrugno et al., Poster presented at the 2016 ASM Microbe, Boston MA, Jul. (Year: 2016).*
510(k) Summary Puritan Liquid Amies Collection and Transport System, https://www.accessdata.fda.gov/cdrh_docs/pdf12/K120846. pdf, pp. 1-7, Jun. 8, (Year: 2012).*
Standard Operating Procedures (SOPs)., Laboratorio de Geromica Viral y Humana, Facultad de Medicina USASLP, pp. 1-4, created and posted Jan. (Year: 2016).*
International Preliminary Search Report and Opinion for Application No. PCT/US2020/49044 dated Feb. 4, 2021.
Supplemental Search Report for Application No. EP 22182987.2 dated Oct. 5, 2022.
Supplemental Exam Report for Application No. EP 22182987.2 dated Oct. 5, 2022.
Examination Report for CA Application No. 3,150,899 dated Jul. 7, 2023.
Supplemental Search Report for Application No. EP 20864758.6 dated Aug. 11, 2023.
Supplemental Exam Report for Application No. EP 20864758.6 dated Aug. 11, 2023.

* cited by examiner

*Primary Examiner* — Cynthia B Wilder
(74) *Attorney, Agent, or Firm* — Remenick PLLC

(57) ABSTRACT

The invention is directed to compositions and methods for collecting, transporting, and storing, without refrigeration, biological materials, which may comprise samples of biological, clinical, forensic, and/or environmental origin. These compositions preserve the viability of the collected organisms and/or the RNA/DNA and proteins in the sample composition mixture and permit the long-term storage of samples. Compositions are compatible with subsequent manipulation of the sample, including propagation and culture of the collected microorganisms, or isolation, purification, detection, and characterization of proteins, nucleic acids, and other macromolecules. When the compositions containing microorganisms and any polynucleotides therein are further processed, such as by nucleic acid testing, there is an increased ability to detect, isolate, purify and/or characterize select microbes and their components, such as nucleic acids, when compared to conventional microbial transport media that contain interfering substances and RNA/DNA extraction is not required prior to PCR analysis. In particular, the compositions disclosed allow for the collection, transport and storage of biological samples for extended periods at ambient temperature, while maintaining the integrity of the macromolecules of the sample for subsequent extraction, identification, and quantitation.

22 Claims, No Drawings

MULTIPURPOSE COMPOSITIONS FOR COLLECTING AND TRANSPORTING BIOLOGICAL MATERIAL

REFERENCE TO RELATED APPLICATIONS

This application claims priority to U.S. Provisional Application No. 62/901,342 filed Sep. 17, 2019, and U.S. Provisional Application No. 62/965,380 filed Jan. 24, 2020, each of which is specifically incorporated herein by reference.

BACKGROUND

1. Field of the Invention

The present invention provides compositions and methods for the detection and analysis of nucleic acid from biological samples. In particular, biological samples for detection and analysis contain nucleic acid sequences of respiratory viruses while maintaining microbial structure and the integrity of proteins and other substances present in the sample. Compositions may sterilize the sample or lower the microorganism count and maintain protein structure. Compositions of the invention are compatible with molecular analysis and do not inhibit or impede nucleic acid extraction or analysis such as detection by polymerase chain reaction procedures.

2. Description of the Background

Before the advent of molecular techniques, most clinical diagnostic laboratories employed the sole use of traditional culturing methods that typically require days to weeks for a viral culture—and even longer for bacterial species. Although advances in cell culture have resulted in quicker culturing times, these cell culturing and propagation techniques are used mainly for confirmatory diagnostic purposes and are still viewed as the standard by which other methods are compared. Differing from molecular methods, cell culture techniques require the maintenance of viability of the organism present in a collected sample. Even analysis of cellular components such as blood cells and tissue biopsies often required viable or intact cells. Currently, most laboratories combine various culture and non-culture techniques to optimize analysis of microbes or host cells of a particular pathogen.

Conventional collection and transport media (e.g., viral transport media, microbial or bacterial transport media, parasite transport media, fungal transport media, environmental sample transport media, universal transport media) have traditionally been developed based on cell culture-related requirements or growth requirements of the collected cells or organism(s), rather than for the purpose of molecular techniques, such as isolating or preserving nucleic acids from the sample for subsequent nucleic acid analysis.

Prior collection media that were originally developed solely to maintain the viability of collected specimens until they were cultured in the laboratory. The Centers for Disease Control and Prevention (CDC) require that the collection of respiratory clinical samples including nasal washes, throat swabs and nasopharyngeal swabs, and other biological samples in approved collection mediums referred to as Viral Transport Medium (VTM), or Universal Transport Medium (UTM). Commercially available transport culture media include, for example, Remel's MicroTest™ M4RT®, Copan's Universal Transport Medium (UTM-RT), Becton Dickinson's Universal Viral Transport Medium, and the like.

These media formulations are comprised of proteins, sugars, balanced salts, buffer, and antibiotics/fungicides. The VTM/UTM formulations were originally developed in the 1980's to maintain the viability of collected specimens until they are safely cultured and identified at regional/centralized laboratories. The VTM/UTM was provided in a plastic tube containing a fluid volume of 1-3 mL medium. Typically a swab with broken off in the tube or alternatively the user adds 0.1 to 1 mL of nasal/oral secretion to the medium and the tubes are shipped to diagnostic laboratories for testing. These molecular transport media were not formulated with the consideration that, in addition to traditional viral propagation and cell culture methodologies, a large portion of microbial identification and analysis done today employs molecular assays, commonly referred to as nucleic acid testing (NAT).

The field of clinical diagnostics changed drastically with the advent of polymerase chain reaction (PCR), and subsequently, real-time PCR (qPCR). qPCR can deliver superior sensitivity and specificity results in hours. Thus, the majority of current diagnostic laboratories have transitioned from traditional culture to qPCR and other rapid nucleic acid testing. A major limitation with commercial UTM/VTMs is they are routinely subjected to NAT in addition to being utilized in culture. Reductions in qPCR cycle threshold (CT) (~3-4 CT values, or ~10-fold difference) during q-PCR have been observed from equal amounts of whole influenza virus extracted from commercial VTM when compared to PRIMESTORE® Molecular Transport Medium (MTM). PRIMESTORE® MTM (PS-MTM) is an FDA-cleared, commercial alternative to UTM/VTM that was designed specifically for qPCR and NAT. PRIMESTORE® MTM inactivates/kills enabling efficient and safe shipping and handling of collected samples It is therefore limited to NAT and cannot be used for propagation of microbes including viruses by standard culture.

Accordingly, there is a need in the art for mixtures, solutions and media that do not substantially interfere with downstream molecular analysis yet maintain the structure of proteins, cell structures and other biological analytes, and/or microbial viability. Such solutions may be used for propagation of microorganisms or molecular assays.

SUMMARY OF THE INVENTION

The present invention overcomes the problems and disadvantages associated with current strategies and designs and provides new tools, compositions and methods for collecting, transporting and storing biological samples preferably for later diagnostic analysis.

One embodiment of the invention is directed to a composition comprising: one or more salts; one or more sugars; one or more buffers; one or more pH indicators; one or more proteins, peptide or amino acids; and one or more antimicrobial agents, wherein the composition contains no gelatin. Preferably, the one or more salts comprises potassium chloride (KCl), calcium chloride ($CaCl_2$), magnesium sulfate ($MgSO_4$), magnesium chloride ($MgCl_2$), potassium phosphate monobasic ($KH_2PO_4$), sodium bicarbonate ($NaHCO_3$), sodium chloride (NaCl), sodium phosphate dibasic ($Na_2HPO_4$), or a combination thereof. Preferably, the one or more sugars comprise a saccharide monomer, a disaccharide, an oligosaccharide, sucrose, fructose, glucose, dextrose, trehalose, galactose, ribose, deoxyribose, maltose, lactose, or a combination thereof. Preferably, the one or more buffers comprise HEPES (4-(2-hydroxyethyl)-1-piperazineethanesulfonic acid), TES (-[[1,3-dihydroxy-2-(hydroxymethyl)propan-2-yl]amino]ethanesulfonic acid), MOPS (3-(N-morpholino)propanesulfonic acid), BES (N,N-bis [2-hydroxyethyl]-2-aminoethanesulfonic acid), TIPSO (3-(N,N-Bis[2-hydroxyethyl]amino)-2-hydroxypropanesulfonic acid, N,N-Bis(2-hydroxyethyl)-3-amino-2-hydroxypropanesulfonic acid), MOBS (4-(N-Morpholino)butanesulfonic acid), Tris-HCl, citrate, MES, Bis-Tris, Bicine, Tricine, ADA, ACES, PIPES, bicarbonate, phosphate, or a combination thereof. Preferably, the one or more pH indicators comprise phenol red (3H-2,1-benzoxathiole 1,1-dioxide), neutral red 3-amino-(7-dimethylamino-2-methylphenazine hydrochloride), or a combination thereof. Preferably, the one or more proteins comprise bovine serum albumin (BSA; acetylated or non-acetylated), L-glutamic acid, L-glutamine, alanyl-1-glutamine, glycyl-1-glutamine, L-cysteine, or a combination thereof. Preferably, the one or more anti-microbial agents comprise colistin, amphotericin B, vancomycin, streptomycin, polymyxin B, or a combination thereof. Preferably, the composition has a pH of from about pH 6.5 to a pH of about 7.5.

Another embodiment of the invention is directed to a composition comprising: one or more chloride salts; one or more phosphate salts; one of more non-ionic detergents; one or more chelators; and one or more lithium salts. Preferably, the one or more chloride salts comprises potassium chloride (KCl), sodium chloride (NaCl), or a combination thereof. Preferably, the one or more phosphate salts comprises potassium phosphate, potassium phosphate monobasic ($KH_2PO_4$), sodium phosphate, sodium phosphate dibasic ($Na_2HPO_4$), or a combination thereof. Preferably, the one or more non-ionic detergents comprises Nonidet P40, TWEEN™, such as TWEEN 20™, TRITON™, such as TRITON X100™, Brij series of detergents, or a combination thereof. Preferably, the one or more chelators comprises ethylene glycol tetra acetic acid, hydroxyethylethylenediaminetriacetic acid, diethylene triamine penta acetic acid, N,N-bis(carboxymethyl)glycine, ethylenediaminetetraacetic, EGTA, HEDTA, DTPA, NTA, EDTA, potassium citrate, magnesium citrate, ferric ammonium citrate, citrate anhydrous, sodium citrate, calcium citrate, ammonium citrate, ammonium bicitrate, citric acid, diammonium citrate, ferric ammonium citrate, lithium citrate, or a combination thereof. Preferably, the one or more lithium salts comprises lithim chloride, lithium phosphate, lithium sulfate, or a combination thereof. Preferably, the composition further comprises one or more antimicrobial agents. Preferably, the one or more antimicrobial agents comprises colistin, amphotericin B, vancomycin, streptomycin, polymyxin B, or a combination thereof.

Another embodiment of the invention comprises a composition disclosed herein further containing a biological sample, wherein the biological sample is suspected of containing a viral, a bacterial, a parasitic or a fungal organism. Preferably the biological sample contains nucleic acid sequences that are characteristic of a respiratory virus or microbial infection. Respiratory viruses that can be detected according the compositions and methods disclosed here include, for example, influenza virus, respiratory syncytial virus, corona virus, parainfluenza virus, adenovirus, rhinovirus, human metapneumovirus, and enterovirus. Microbial infections include, for example, *Mycobacterium* spp. (e.g., *M. tuberculosis, M. smegmatis*), *Streptococcus* spp. (e.g., *S. pneumoniae, S. pyogenes*), and *Corynebacterium* spp. (e.g., *C. diphtheria*).

Another embodiment of the invention comprises methods for transporting a biological sample without refrigeration comprising: collecting a biological sample; combining the biological sample with a composition disclosed herein, wherein nucleic acid sequences and/or protein sequences of the biological sample remain detectable for at least 3-7 days or longer subsequent to combining. Preferably, the collecting and the combining steps are performed at ambient temperature and the resulting mixture is safe for transportation.

Other embodiments and advantages of the invention are set forth in part in the description, which follows, and in part, may be obvious from this description, or may be learned from the practice of the invention.

DESCRIPTION OF THE INVENTION

Standardized procedures for real-time (R) reverse transcription polymerase chain reaction (RT-PCR) testing from respiratory samples typically involve collection in viral transport medium (VTM). For clinical diagnostic testing using RRT-PCR, the World Health Organization (WHO) recommends RRT-PCR analysis on clinical samples collected in Copan's Universal Transport Medium. Transport media (referred to as Universal Transport Medium (UTM) or more commonly, a Viral Transport Medium (VTM), or collection, transport and storage medium (CTS). These mediums are referred to herein as UTM, VTW, CTS or simply transport medium. Transport medium contains reagent blends optimized for preserving and maintaining clinical sample viral viability for downstream culture. Many samples collected in commercial transport media are routinely subjected to RNA/DNA extraction and nucleic acid testing (NAT) such as real-time RT-PCR.

Commercially available transport media comprise complex mixes of ingredients designed to preserve and maintain cell and/or viral viability for downstream culture. These same transport media and considered sufficient for RNA/DNA extraction and subsequent nucleic acid testing (NAT). However, many of these transport media contain compounds that are inhibitory to nucleic acid isolation and/or testing such as subsequent RRT-PCR analysis or other NAT protocols or, in the alternative, do not provide acceptable levels of nucleic acid stability.

New transport media formulation have been surprisingly discovered that serve the functions of maintaining microorganism viability (i.e., the ability to culture collected samples) and/or maintaining the integrity of nucleic acid for subsequent qPCR and other NAT procedures. These new transport medias are free of inhibitors and carry over reagents known to interfere with nucleic acid extraction, qPCR and DNA hybridization, and contain an optimized blend of ingredients for specimen collection and transport at ambient temperatures.

Biological Specimen Collection and Handling

Collection of a biological sample or specimen is a first step in many diagnostic platforms, propagation techniques, and molecular protocols requiring the isolation, detection and analysis of potentially minute amounts of nucleic acids from human or animal tissues, or microorganisms including, but not limited to, bacteria, fungi and viruses. Preferably the biological sample contains nucleic acid sequences that are characteristic of a respiratory virus. Respiratory viruses that can be detected according the compositions and methods disclosed here include, for example, influenza virus, respiratory syncytial virus, corona virus, parainfluenza virus, adenovirus, rhinovirus, human metapneumovirus, and enterovirus. To facilitate the application of microbial detection and diagnostic strategies and their integration into the mainstream diagnostic laboratories there is a need for reliable, robust, and standardized collection systems developed specifically with the intent of being utilized for downstream processing such as nucleic acid based detection and testing, propagation of viral or microbial specimens in culture or both. The present invention affords such improvements through the use of new transport media and formulations that display significant advantages over many of the commercially-available tissue or microorganism transport media.

Biological samples in the practice of the invention can be obtained fresh, or can be obtained after being stored for a period of time, and may include, for example, material(s) of a clinical, veterinary, environmental or forensic origin, or may be isolated from one or more sources, such as without limitation, foods and foodstuffs, beverages, and beverage ingredients, animal feed and commercial feedstocks, potable waters, wastewater streams, runoff, industrial wastes or effluents, natural water sources, groundwater, soils, airborne sources, or from pandemic or epidemic populations, epidemiological samples, research materials, pathology specimens, suspected bioterrorism agents, crime scene evidence, and the like.

Exemplary biological samples include, but are not limited to, whole blood, plasma, serum, sputum, urine, stool, white blood cells, red blood cells, buffy coat, swabs (including, without limitation, buccal swabs, throat swabs, vaginal swabs, urethral swabs, cervical swabs, rectal swabs, lesion swabs, abscess swabs, nasopharyngeal swabs, and the like), urine, stool, sputum, tears, mucus, saliva, semen, vaginal fluids, lymphatic fluid, amniotic fluid, spinal or cerebrospinal fluid, peritoneal effusions, pleural effusions, exudates, punctates, epithelial smears, biopsies, bone marrow samples, fluid from cysts or abscess contents, synovial fluid, vitreous or aqueous humor, eye washes or aspirates, pulmonary lavage or lung aspirates, and organs and tissues, including but not limited to, liver, spleen, kidney, lung, intestine, brain, heart, muscle, pancreas, and the like, and any combination thereof. In some embodiments, the sample may be, or be from, an organism that acts as a vector, such as a mosquito, or tick, or other insect(s). Preferably the biological sample comprises cells suspected of being infected with a pathogen and the pathogen is a viral, a bacterial, a parasitic or a fungal infection.

Examples of pathogens or target organisms to be detected include, for example, virus, bacteria, fungus, and parasites. Bacteria include *Mycobacterium tuberculosis, Streptococcus* spp., *Pseudomonas* spp., *Shigella* spp., *Yersinia* spp. (e.g., *Y. pestis*), *Clostridium* spp. (e.g., *C. botulinum, C. difficile*), *Listeria* spp., *Staphylococcus* spp., *Salmonella* spp., *Vibrio* spp., *Chlamydia* spp., *Gonorrhea* spp., *Syphilis* spp., MRSA, *Streptococcus* spp. (e.g., *S. pneumoniae, S. pyogenes*), *Escherichia* spp. (e.g., *E. coli*), *Pseudomonas* spp., *Aeromonas* spp., *Citrobacter* spp (e.g., *C. freundii, C. braaki*), *Proteus* spp., *Serratia* spp., *Klebsiella* spp., *Enterobacter* spp., *Chlamydophila* spp., *Mycobacterium* spp. (e.g., *M. tuberculosis M. smegmatis*), MRSA (Methicillin-resistant *Staphylococcus aureus*), *Corynebacterium* spp. (e.g., *C. diphtheria*), and *Mycoplasma* spp. (e.g., *Ureaplasma parvum, Ureaplasma urealyticum*). Virus include influenza virus, Corona virus, Adenovirus, Respiratory Syncytial virus, Zika virus, Rubella virus, Hepatitis virus, Herpes Simplex virus, retrovirus, varicella zoster virus, human papilloma virus, parvovirus, parainfluenza virus, rhinovirus, human metapneumovirus and enterovirus, and HIV. Parasitic organisms include, for example, *Plasmodium* spp., *Leishmania* spp., Guardia spp., endoparasites, protozoan, and helminth spp. Fungal organisms include, for example, *Cryptococci, aspergillus* and *candida*. Diseases caused by microbes to which the compositions and methodology can be applied include sepsis, colds, flu, gastrointestinal infections, sexually transmitted diseases, immunodeficiency syndrome, nosocomial infections, Celiac disease, inflammatory bowel disease, inflammation, multiple sclerosis, auto-immune disorders, chronic fatigue syndrome, Rheumatoid arthritis, myasthenia gravis, Systemic lupus erythematosus, and infectious psoriasis.

Exemplary Formulations of VTM

One embodiment of the invention is directed to viral transport media ("VTM"). VTM formulations of the disclosure preserve virus that may be present in the biological specimen without interfering with downstream molecular detection such as DNA and/or RNA extraction, qPCR, next generation sequencing, etc. Preferred formulations allow for virus culture. Preferred VTM contains one or more salts, one or more sugars, one or more buffers, one or more pH indicators, one or more anti-microbial agents, and one or more proteins, peptide or amino acids, at low levels, but in the absence of a gelatin. The pH range of VTM is from about pH 6.0 to a pH of about 8.0, preferably from about pH 6.5 to a pH of about 7.5, and more preferably from about pH 7.0 to a pH of about 7.5. Preferred formulations may be protein-free and/or contain no gelatin, BSA, and/or supplemental amino acids known to inhibit downstream extraction and molecular methods.

Preferred salts used in VTM include, for example, potassium chloride (KCl), calcium chloride ($CaCl_2$), magnesium sulfate ($MgSO_4$), magnesium chloride ($MgCl_2$), potassium phosphate monobasic ($KH_2PO_4$), sodium bicarbonate ($NaHCO_3$), sodium chloride (NaCl), sodium phosphate dibasic ($Na_2HPO_4$), and combinations thereof. Preferred sugars used in VTM include, for example, monomers, disaccharides, polymers, and combinations thereof, or sucrose, fructose, glucose, dextrose, trehalose, galactose, ribose, deoxyribose, maltose, lactose, and combinations thereof. Preferred buffers used in VTM include, for example, HEPES (4-(2-hydroxyethyl)-1-piperazineethanesulfonic acid), TES (-[[1,3-dihydroxy-2-(hydroxymethyl)propan-2-yl]amino]ethanesulfonic acid), MOPS (3-(N-morpholino)propanesulfonic acid), BES (N,N-bis[2-hydroxyethyl]-2-aminoethanesulfonic acid), TIPSO (3-(N,N-Bis[2-hydroxyethyl]amino)-2-hydroxypropanesulfonic acid, N,N-Bis(2-hydroxyethyl)-3-amino-2-hydroxypropanesulfonic acid), MOBS (4-(N-Morpholino)butanesulfonic acid), Tris-HCl, citrate, MES, Bis-Tris, Bicine, Tricine, ADA, ACES, PIPES, bicarbonate, phosphate, and combinations thereof. Also preferably, the pKa of the buffer is within a value of 1.0 pH unit of the pH of the meiad, more preferably within about 0.5 pH units, more preferably within about 0.2 pH units, and more preferably when pKa and pH are equivalent. Also preferred is wherein the variance (i.e., plus 1 pH unit or minus 1 pH unit) is biased towar the buffering capacity. Preferred proteins, peptide and aminos acids used in VTM include, for example, bovine serum albumin (BSA; acetylated or non-acetylated), L-glutamic acid, L-glutamine, alanyl-1-glutamine, glycyl-1-glutamine, L-cysteine, and combinations thereof. Preferred pH indicators used in transport media include, for example, phenol red (3H-2,1-benzoxathiole 1,1-dioxide), neutral red 3-amino-(7-dimethylamino-2-methylphenazine hydrochloride) and combinations thereof. One or more anti-microbial agents, although optional in transport media may be anti-bacterial, anti-parasitic, and/or anti-fungal, largely depending on the particular biological specimen. For example, when isolating fungal organisms, useful anti-microbial agents may be anti-bacterial agents. When isolating virus, useful anti-microbials may be anti-fungal and anti-bacterial agents. Selected examples that may be used include, but are not limited to colistin, amphotericin B, vancomycin, streptomycin, polymyxin B, and combinations thereof.

Preferably, the total salt concentration in VTM is from about 0.1% to about 1.0%, the total sugar concentration is from about 2% to about 10%, the total protein concentration is from about 0.2% to about 1.0%, the total buffer concentration is from about 0.2% to about 1.0%, the total pH indicator concentration is from about 0.0001% to about 0.001%, and the total anti-microbial concentration is from about 0.00001% to about 0.001%, or at the manufacturer recommended concentration for the microbial.

One preferred VTM comprises sucrose at about 25 g, fructose at about 25 g, glucose at about 25 g, MgSO4 at about 0.25 g, CaCl2 at about 0.3 g, BSA at about 5.0 g, L-glutamic acid at about 0.5 g, L-glutamine at about 0.5 g, HEPES at about 6.0 g, phenol red at about 10.0 mg, amphotericin at about 1.0 mg, and polymyxin B at about 2.0 mg, all of which are dissolved to completion in one liter of deionized, distilled and/or nuclease-free water and the pH adjusted to about 7.3 (+/−0.1) using HCL. Another preferred VTM contains 0.8×HBSS. 0.6% Hepes Buffer (w/v), 5.0% sucrose (w/v), 0.1% glycerol (v/v), 0.2 μg/mL amphotericin B, 5.0 μg/mL polymyxin B, and 2.0 0 μg/mL vancomycin.

Exemplary Formulations of ATM

Another embodiment of the invention is directed to analyte transport media (ATM). ATM of this disclosure can be utilized for combining with biological samples for analyte and/or drug testing and optionally includes antibodies and/or proteins. Preferably, ATM comprises one or more chloride salts, one or more phosphate salts, one of more non-ionic detergents, one or more chelators, a lithium salt, and, optionally, one or more antimicrobial agents. The pH range of ATM is from about pH 6.0 to a pH of about 8.0, preferably from about pH 6.5 to a pH of about 7.5, and more preferably from about pH 7.0 to a pH of about 7.5.

Preferred chloride salts used in ATM include, for example, potassium chloride (KCl), sodium chloride (NaCl), and combinations thereof. Preferred phosphate salts used in ATM include, for example, potassium phosphate such as potassium phosphate monobasic ($KH_2PO_4$), sodium phosphate such as sodium phosphate dibasic ($Na_2HPO_4$), and combinations thereof. Preferred non-ionic detergents used in ATM include, for example, Tween compounds, such as but not limited to TWEEN 20™, TWEEN 40™, TWEEN 60™, TWEEN 68™, and TWEEN 80™, TRITON™, such as but not limited to TRITON n57™, TRITON n60™, TRITON X45™ TRITON X100™, TRITON X102™, TRITON X114™, TRITONX165™, TRITON X305™ TRITON X405™, a nonidet compound such as but not limited to nonidet P40 and nonidet P60, a Brij compound such as but not limited to Brij-35, Brij 58, Brij L23, Brij 010, glycerol compounds, glucopyranoside compounds, glucosime compounds, a saponin compound, detergents based on polyoxyethylene or a glycoside such as but not limited to ethoxylates or PEGylates and their metabolites, nonylphenol, and combinations thereof. Additional examples include octyl thioglucoside and maltosides, the HEGA and MEGA series detergents, possessing a sugar alcohol as headgroup. Preferred lithium salts used in ATM include, for example, lithim chloride, lithium phosphate, lithium sulfate, and combinations thereof. Preferred chelators used in ATM include, for example, ethylene glycol tetra acetic acid, hydroxyethylethylenediaminetriacetic acid, diethylene triamine penta acetic acid, N,N-bis(carboxymethyl)glycine, ethylenediaminetetraacetic, EGTA, HEDTA, DTPA, NTA, EDTA, potassium citrate, magnesium citrate, ferric ammonium citrate, citrate anhydrous, sodium citrate, calcium citrate, ammonium citrate, ammonium bicitrate, citric acid, diammonium citrate, ferric ammonium citrate, lithium citrate, and combinations thereof. One or more anti-microbial agents, although optional in transport media may be anti-bacterial, anti-parasitic, and/or anti-fungal, largely dependeing on the particular biological specimen.

Preferably, the total chloride salt concentration in ATM is from about 0.1% to about 0.5%, the total phosphate salt concentration is from about 0.05% to about 0.1%, the total non-ionic detergent (e.g. with uncharged, hydrophilic headgroups) concentration is from about 0.5% to about 1.0%, the total chelator concentration is from about 0.005% to about 0.01%, the total lithium salt concentration used in ATM is from about 0.001% to about 0.01%.

One preferred ATM comprises sodium chloride at about 4 g, potassium chloride at about 0.1 g, disodium phosphate at about 0.72 g, monopotassium phosphate at about 0.12 g, Tween 20 at about 4 ml, Triton-X, Tween or a Brij detergent at about 4 ml, EDTA at about 60 mg, lithium chloride at about 0.21 g, all of which are dissolved to completion in one liter of deionized, distilled and/or nuclease-free water and the pH adjusted to about 7.3 (+/−0.1) using HCL. Another preferred ATM formulation comprises 0.5×PBS, 0.5% Tween-20 (v/v), 0.5% Triton-X (v/v), 2 mM EDTA (molarity), 5 mM LiCl (molarity). Additionally, an antifoaming agent such as Antifoam A solution, can be utilized in the final formulation to prevent against excessive bubbling/foaming. The concentration of the antifoaming agent is ideally 50 parts per million (ppm) but a range between 1-200 ppm is suitable. Preferably the components are combined in a clean and sterile beaker containing a sterile stir magnet and maintained on low or medium heat with gentle stirring.

Combining Biological Samples with Transport Media

VTM and ATM of the invention can be used for the collection and transport of biological samples for processing to detect microorganisms, proteins, macromolecules, or other substances suspected of being present in the sample. Testing of samples in VTM is generally for microbial culture and nucleic acid extraction, amplification, sequencing and characterization. Testing of samples in ATM is generally for detection of proteins and/or other substances and the cultivation of selected microbes. Detectable microbes include infectious agents, parasites, virus (e.g., Influenza, Coronavirus, Herpes virus, etc.), bacteria (e.g., MTB, *Streptococcus*, Pertussis, etc.), genetic markers in host, mammalian, pathogenic, or other genomes (e.g., defects, mutations, familial markers), and identification of a specific microorganism to include molecular analysis. The media preserves the selected microorganisms at ambient temperature for extended periods, such as hours to days, until the organisms are subjected to culture. There is also no need for an extraction step.

Transport media of the invention stabilize the nucleic acid and/or proteins of the sample and contain no ingredients that would interfere with NAT and other molecular analyses. Alternatively, potentially interfering substances in the biological sample may be removed by pre-processing as necessary by molecular techniques such as, for example, dialysis, salt or acid extraction, chromatography techniques, or other methods well known in the art.

In some embodiments the collection and transport medium is compatible with downstream processing and analyzing of pathogens, preferably human pathogens. In particular embodiments, the collection and transport medium is able to collect, store and/or transport samples containing, for example, *M. tuberculosis, Chlamydia, Mycoplasma, Ureaplasma*, or viruses such as Adenovirus, Influenza virus or RSV, or any combination thereof, including without limitation, to predict and help manage shift and drift and to manage an imminent or ongoing pandemic. In some embodiments, the collecting and transporting medium is capable of maintaining the viability of the microorganisms contained therein until the microorganism of interest is able to be cultured.

In certain embodiments, the collection, transport or storage medium is compatible with the isolation or purification of one or more nucleic acids from the biological sample and the performance of at least a first thermal cycling reaction on at a least a first nucleic acid so isolated or purified. A thermal cycling reaction can include, without limitation, PCR-based methodologies, as well as the addition of thermal cycling reaction reagents, heating or cooling phases, the amplification of a population of polynucleotides, the maintenance of a particular temperature, and the collection of a thermal cycling or amplification product. For example, a significant reduction (3-4 CT, or 10-fold differences) in cycle threshold (CT) values during RRT-PCR was observed when equal amounts of whole influenza virus were extracted from commercial UTM compared to VTM as disclosed herein.

The collection and transport media of the present invention provides a number of improvements and benefits over those presently available in the art. Exemplary benefits include, without limitation, one or more of the following: compatibility with a variety of conventional nucleic acid extraction, purification, and amplification systems, genomic or meta-genomic analysis (e.g., sequencing), and any other suitable methods and techniques; compatibility with conventional microbial culturing techniques for propagation purposes; preservation of nucleic acid integrity within the sample; maintenance of high-quality, high-fidelity populations of nucleic acids during downstream molecular or chemical detection, analysis, or characterization of the medium containing the biological sample; facilitation of transport and shipping of the medium contacted with the biological sample at ambient temperatures, even over extended periods of time, or extreme temperature variations; suitability for short-(several hours to several days), intermediate-(days to several weeks), or long-(weeks to several months) term storage of the isolated nucleic acids.

In one aspect of the invention, the present invention provides for a medium that, when contacted with a sample, enables the rapid detection of a particular polynucleotide sequence. In an overall and general sense, the medium contacted with the sample allows for amplification of a population of polynucleotides suspected of containing the particular sequence of interest using conventional methods such as PCR and forward and reverse primers that are specific for the target sequence, hybridization of a specific probe set with the resulting PCR product, and performing analysis such as melting curve analysis. The present invention also concerns nucleic acid compositions, including, without limitation, DNA, RNA and PNA, isolatable from one or more biological samples or specimens using the collection, storage and transport medium of the invention.

In some embodiments of the compositions and methods of the present invention, the molecular and/or chemical detection, analysis, or characterization of the sample contacted with the VTM or ATM medium of the present invention is not substantially interfered with or inhibited by interfering substances contained in the VTM or ATM medium. In some embodiments, when the sample contacted with the VTM or ATM medium of the present invention is processed, there is at least an about 10 percent improvement as compared to when similar or the same type of samples contacted with conventional media are processed. In other embodiments there is at least about an 8 percent improvement, at least about a 6 percent improvement, and in some instances at least about a 5 percent, 4 percent, 3 percent, 2 percent or 1 percent improvement over when conventional medium is used.

Molecular Analyses

A biological sample may contain or be presumed to contain one or more microorganisms, drugs, and or chemicals of interest. It thus contains tissue, cells, microbes, nucleic acids, proteins, carbohydrates, lipids, biochemicals, and other molecules and substances of interest (e.g., drugs, chemicals). The nucleic acids include genomic DNA, RNA, mRNA, tRNA (all which can be genetically engineered to cDNA).

Nucleic acids obtained from biological samples collected, stored, or transported in one of the compositions of the invention are advantageously compatible with a number of conventional molecular and diagnostic isolation, purification, detection, and/or analytic methodologies (e.g., PCR, RT-PCR, qPCR, real time PCR, Loop-mediated isothermal amplification (LAMP), fragment analysis, traditional and next generation sequencing, etc.).

The compositions of the invention facilitate recovery, storage, and transport of populations of stabilized, substantially non-degraded proteins, other substances and molecules and/or polynucleotides for use in a variety of downstream analyses including, without limitation, nucleic acid isolation, purification, amplification, and molecular analytical and/or diagnostic testing, assay, analysis, or characterization, and the like.

In certain embodiments, the nucleic acid(s) isolated by the methods of the present invention may serve as a template in one or more subsequent molecular biological applications, assays, or techniques, including, without limitation, genetic fingerprinting; amplified fragment length polymorphism (AFLP); restriction fragment length polymorphism analysis (RFLP); allele-specific oligonucleotide analysis (ASOA); microsatellite analysis; Southern hybridization; Northern hybridization; variable number of tandem repeats PCR (VNTR-PCR); dot-blot hybridization; PCR; quantitative real-time PCR; polymerase cycling assembly (PCA); nested PCR; quantitative PCR (Q-PCR); asymmetric PCR; DNA footprinting; single nucleotide polymorphism (SNP) genotyping; reverse transcription PCR (RT-PCR); multiplex PCR (m-PCR); multiplex ligation-dependent probe amplification (MLPA); ligation-mediated PCR (LmPCR); methylation specific PCR (MPCR); helicase-dependent amplification (HDA); overlap-extension PCR (OE-PCR); whole-genome amplification (WGA); direct DNA sequencing by Sanger, or next-generation sequencing using either short read or long read methods, plasmid isolation; allelic amplification; site-directed mutagenesis; high-throughput genetic screening; or the like, or any combination thereof.

A number of template dependent processes are available to amplify the marker sequences present in a given template sample. One of the best-known amplification methods is the polymerase chain reaction (referred to as PCR) which is described in detail e.g., in U.S. Pat. Nos. 4,683,195, 4,683, 202 and 4,800,159 (each of which is specifically incorporated herein in its entirety by express reference thereto. Another method for amplification is the ligase chain reaction ("LCR"), disclosed, e.g., in EPA No. 320 308, and U.S. Pat. No. 4,883,750, each of which is incorporated herein in its entirety by express reference thereto. An isothermal amplification method, in which restriction endonucleases and ligases are used to achieve the amplification of target molecules that contain nucleotide 5'[α-thio]-triphosphates in one strand of a restriction site may also be useful in the amplification of nucleic acids in the present invention.

Sample Collection Systems and Diagnostic Kits

In the practice of the invention, the disclosed compositions may be used in a variety of sample collection systems. Exemplary such systems may incorporate one or more collection devices (e.g., a swab, curette, culture loop, etc.); and a collection vessel (e.g., a vial, ampule, flask, bottle, syringe, test tube, specimen cup, spit-tube device, etc.) to contain one or more of the compositions disclosed herein, and subsequently store and/or transport the collected sample. Exemplary specimen collection devices include, without limitation, those described in one or more of U.S. Pat. Nos. 4,235,244; 4,707,450; 4,803,998; 5,091,316; 5,108,927; 5,163,441; 6,312,395; 7,311,671; 7,541,194; and 7,648,681 (each of which is specifically incorporated herein in its entirety by express reference thereto).

The collection vessel is preferably releasably openable, such that it can be opened to insert the one-step compositions and closed and packaged, opened to insert the sample and optionally a portion of the collection device and closed for storage and transport, or both. The collection vessel may use any suitable releasably openable mechanism, including without limitation a screw cap, snap top, press-and-turn top, or the like. Such systems may also further optionally include one or more additional reagents, storage devices, transport devices, and/or instructions for obtaining, collecting, transporting, or assaying one or more samples in such systems.

The following examples illustrate embodiments of the invention but should not be viewed as limiting the scope of the invention.

EXAMPLES

Example 1 Preparations of Transport Media

Preparation of VTM

VTM of this disclosure can be simply prepared by combining and pooling ingredients:
1. A mixture of salts.
2. One or more sugars that may be monomers, disaccharides, or polymers.
3. One or more buffers.
4. Optionally one or more low level proteins.
5. Optionally a pH indicator.
6. One or more antimicrobial agent.
7. pH: 6-8 and preferably ~7 (+/−0.1)
8. In the absence of any gelatins, proteins or amino acids that are known to inhibit downstream extraction and/or molecular testing.

Exemplary salts include: KCl, $CaCl_2$, $MgSO_4$, $MgCl_2$, Potassium Phosphate monobasic ($KH_2PO_4$), Sodium Bicarbonate ($NaHCO_3$), Sodium Chloride (NaCl), Sodium Phosphate dibasic ($Na_2HPO_4$), Hanks Balanced Salt Solution (HBSS).

Exemplary Sugars include (monomers, disaccharides, polymers or combinations therein): Sucrose, fructose, glucose, dextrose, trehalose, galactose, ribose, deoxyribose, maltose, lactose Exemplary Buffers include: HEPES (4-(2-hydroxyethyl)-1-piperazineethanesulfonic acid), TES (-[[1,3-dihydroxy-2-(hydroxymethyl)propan-2-yl]amino]ethanesulfonic acid), MOPS (3-(N-morpholino)propanesulfonic acid), BES (N,N-bis[2-hydroxyethyl]-2-aminoethanesulfonic acid), TIPSO (3-(N,N-Bis[2-hydroxyethyl]amino)-2-hydroxypropanesulfonic acid, N,N-Bis(2-hydroxyethyl)-3-amino-2-hydroxypropanesulfonic acid), MOBS (4-(N-Morpholino)butanesulfonic acid).

Exemplary Proteins include: Bovine Serum Albumin (BSA; acetylated or non-acetylated), mammalian albumin, fish-derived albumin, L-Glutamic acid, L-Glutamine, alanyl-1-glutamine and glycyl-1-glutamine, L-cysteine.

A pH indicator includes: Phenol Red (3H-2,1-Benzoxathiole 1,1-dioxide) or Neutral Red 3-Amino-(7-dimethyl-amino-2-methylphenazine hydrochloride).

Exemplary Antimicrobials include: Colistin, amphotericin B, vancomycin, streptomycin, polymyxin B.

Preferred formulations for VTM are shown in Table 1

TABLE 1

| Component | Amount |
|---|---|
| VTM Formulation A | |
| Sucrose | 25.0 g |
| Fructose | 25.0 g |
| Glucose | 25.0 g |
| MgSO4 | 0.25 g |
| CaCl2 | 0.3 g |
| BSA | 5.0 g |
| L-Glutamic acid | 0.5 g |
| L-Glutamine | 0.5 g |
| HEPES | 6.0 g |
| Phenol Red | 10.0 mg |
| Amphotericin B | 1.0 mg |
| Polymyxin B | 2.0 mg |
| Adjust pH to 7.3 (+/−0.1) using HCL Combined with deionized, distilled, and nuclease-free water up to one liter. | |
| VTM Formulation B | |
| HBSS | 400 mL |
| Sucrose | 25.0 g |
| Glycerol | 0.5 mL |
| HEPES | 3.0 g |
| Amphotericin B | 1.0 mg |
| Polymyxin B | 25.0 mg |
| Vancomycin | 10.0 mg |
| Adjust pH to 7.2 (+/−0.1) using NaOH (~40-50 µl) Combined with deionized, distilled, and nuclease-free water up to 500 mL. | |

Preferred formulations for ATM are shown in Table 2.

TABLE 2

| ATM Formulation A | | ATM Formulation B | |
|---|---|---|---|
| Component | Amount | Component | Amount |
| NaCl | 4.0 grms | TWEEN-20 ™ | 5 mL |
| KCl | 0.1 grms | TRITON X ™ | 5 mL |
| Disodium phosphate | 0.72 grms | EDTA | 0.4 mL (0.5M) |
| Monopotassium phosphate | 0.12 grms | LiCl | 0.21 grms |

TABLE 2-continued

| | | | |
|---|---|---|---|
| TWEEN-20 ™ | 4 mL | PBS | 500 mL (1 × pH 7.4) |
| TRITON X ™ | 4 mL | Adjust pH to 7.4 (+/−0.1) with conc. HCl | |
| (0.5M) EDTA | 0.4 mL | q.s. to 1 liter with nuclease-free water. | |
| Lithium chloride | 0.21 grms | | |
| Adjust pH to 7.3 (+/−0.1) using HCL | | | |
| q.s. with deionized, distilled, and | | | |
| nuclease-free water to one liter. | | | |

ATM Formulation C

| Component | Amount |
|---|---|
| 1 × PBS (pouches) | 0.5× |
| LiCl (grams) | 5 mM |
| TWEEN-20 ™ (mL) | 0.50% |
| TRITON X ™ (mL) | 0.50% |
| 0.5M EDTA (mL) | 2 mM |
| Antifoan A (mL) | 50 ppm |
| Adjust pH to 7.4-7.8 and again to pH 7.2 (+/−0.2) | |
| q.s. with deionized, distilled, and nuclease-free water. | |

Key features of ATM formulations:
- For collection/transport/detection of proteins and biological analytes
- Preserve/stabilize 'naked' bioanalytes from collected samples, i.e., buccal, oral etc.
- Compatible with commercial Rapid Antigen Tests (Remel, BD, Quidel, others)
- Suitable for diagnostic tests for DNA/RNA detection (qPCR, Next-Gen Sequencing)
- ATM is a mild preservation solution free of hazardous, toxic, or flammable reagents Both ATM and VTM are formulated to provide sensitive PCR as well as preserve other molecules such as proteins or in the case of VTM allow preservation of live virus (Flu) for culture. The use of VTM or ATM allow for shipping of biological samples at ambient temperatures without compromising sample integrity or the fidelity of nucleic acid detection and identification.

Example 2 Test of Viability of Influenza a Virus in VTM as Compared to UTM

VTM was superior to Copan UTM. The data for VTM compared to Copan UTM showing that VTM actually grew virus at 1 µl (low) H1N1 concentration when Copan did not. Specimens were transported at ambient temperature overnight to Gaithersburg, MD from San Antonio, TX and then within 1-2 days cultured for influenza and TCID50/ml calculated (1 ml sample in 50 ml of total volume). Results are shown in Table 3.

TABLE 3

| Sample | TCID50 | Sample Description |
|---|---|---|
| 1 | 0.00E+00 | VTM Media-NTC |
| 2 | 3.16E+07 | VTM Media-25 µl (high) H1N1 |
| 3 | 4.64E+05 | VTM Media-10 µl (high) H1N1 |
| 4 | 0.00E+00 | Copan-NTC |
| 5 | 0.00E+00 | Copan UTM-1 µl (low) H1N1 |
| 6 | 3.16E+06 | Copan UTM-10 µl (low) H1N1 |
| 7 | 1.00E+06 | VTM Media-10 µl (med) H1N1 |
| 8 | 4.64E+05 | VTM Media-1 µl (low) H1N1 |
| 9 | 4.64E+05 | VTM Media-1 µl (low) H1N1 |
| 10 | 1.00E+06 | VTM Media-10 µl (med) H1N1 |
| VE | 0.00E+00 | TCPK Media |

Example 3 ATM Kills Viruses

Influenza A is a major human pathogen that causes global epidemics and pandemics. ATM maintains protein integrity and preserve RNA and DNA for days at ambient temperature, while killing and inactivating bacteria and viruses (see Tables 4 and 5). Influenza A was used as a model to demonstrate the viral killing capabilities of ATM. While the TWEEN 20™ reduced tissue culture cells adherence to the flask at 1:25 and 1:50 dilution (Table 5), the virus was killed (6-7 logs) after 20 minutes in ATM at all dilutions.

TABLE 4

Test of Viability of ATM Flu Study

| Serial Dilution | Sample | Contents | TCID50/ml |
|---|---|---|---|
| 1:25 | 1 | ATM only | 0.00E+00 |
| 1:25 | 2 | Virus only | 4.64E+06 |
| 1:25 | 3 | Virus + ATM | 0.00E+00 |
| 1:50 | 4 | ATM only | 0.00E+00 |
| 1:50 | 5 | Virus only | 1.00E+07 |
| 1:50 | 6 | Virus + ATM | 0.00E+00 |
| 1:100 | 7 | ATM only | 0.00E+00 |
| 1:100 | 8 | Virus only | 1.00E+07 |
| 1:100 | 9 | Virus + ATM | 0.00E+00 |
| 1:1000 | 10 | ATM only | 0.00E+00 |
| 1:1000 | 11 | Virus only | 1.47E+05 |
| 1:1000 | 12 | Virus + ATM | 0.00E+00 |

Virus = Hong Kong stock conc. @ $10^8$ with 20 minute incubation time for virus plus ATM

TABLE 5

| Serial Dilution | Cell Adherence |
|---|---|
| 1:25 | No adherence |
| 1:50 | Partial Adherence 75% |
| 1:100 | Adherence 100% |
| 1:1000 | Adherence 100% |

Example 4 Adenovirus-PCR and Rapid Antigen Comparison to Copan

Three different storage media were tested for stability of Adenovirus DNA, Copan UTM and VTM and ATM of this disclosure. Stock Adeno (type 14) was used to spike media at three clinically relevant concentrations. Nucleic acid extraction and qPCR analysis were performed as previously described. Rapid antigen testing was performed using SAS™ Adeno Test (SA Scientific, San Antonio, TX). Table 6 shows that clinically relevant concentrations.

TABLE 6

| Spike-In Organism | Organism Type | Concentration | Clinical Relevancy |
|---|---|---|---|
| Adenovirus (type 14) | (−) ss DNA virus | $10^3$ copies | Low |
| Adenovirus (type 14) | (−) ss DNA virus | $10^6$ copies | Medium |
| Adenovirus (type 14) | (−) ss DNA virus | $10^8$ copies | High |

Experiments were repeated twice and averaged. The limit of detection of qPCR assay with PrimeMix is about $10^9$ to $10^1$ PFU/ml. The results achieved are shown in Table 7.

TABLE 7

| Detection | Rep1 | Rep2 | Average | SD |
|---|---|---|---|---|
| $10^9$ copies | 14.5 | 14.7 | 14.6 | 0.14 |
| $10^8$ copies | 17.3 | 16.7 | 17.0 | 0.42 |
| $10^6$ copies | 22.1 | 21.9 | 22.0 | 0.14 |
| $10^3$ copies | 28.6 | 28.4 | 28.5 | 0.14 |
| $10^2$ copies | 33.2 | 33.4 | 33.3 | 0.14 |
| $10^1$ copies | 40.0 | 39.2 | 39.6 | 0.57 |

$Y = 5.1543x + 7.7933 || R^2 = 0.9865$

For each Adenovirus concentration, (high, medium, low), the qPCR Ct values was lower (i.e., optimal) for samples extracted and detected from ATM and UTM as compared to Copan UTM (see Table 8).

TABLE 8

| Detection | ATM | VTM | Copan UTM |
|---|---|---|---|
| High | 17.2 | 23.1 | 29.4 |
| Medium | 17.4 | 23.8 | 31.9 |
| Low | 18.4 | 25.4 | 33.6 |

Using Rapid Antigen Testing, all mediums were equivalent and detection high and medium concentrations low. Low concentrations ($10^3$ PFU/ml) were below the limit of detection for rapid antigen testing. Two tests for each sample were performed. Results were visualized/verified 15 minutes and one hour after initiation. Table 9 shows the results following this SAS Adeno testing:

TABLE 9

| Detection | ATM | VTM | Copan UTM |
|---|---|---|---|
| High | Pos/Pos | Pos/Pos | Pos/Pos |
| Medium | Pos/Pos | Pos/Pos | Pos/Pos |
| Low | Neg/Neg | Neg/Neg | Neg/Neg |

As is clear from the data, ATM and VTM of this disclosure exhibited enhanced detection of viral DNA at high, medium, and low concentrations compared to Copan UTM as assessed by cycle threshold (Ct) real-time qPCR values. ATM and VTM provided equivalent results as compared to Copan UTM as assessed by SAS Adeno rapid antigen testing. Clinical specimens collected in ATM and VTM are compatible with rapid antigen lateral flow tests. ATM or VTM is the ideal medium for a single, collected clinical sample that requires additional multiple molecular testing approaches such as qPCR, NGS, etc.

Example 5 ATM Comparison to Copan UTM with Stock Flu Viruses

Two different storage media were tested for stability of Flu viruses, namely Copan UTM and ATM. Stock Flu viruses were used to spike media (2) prior to: (A) nucleic acid extraction and qPCR analysis (PXT and PrimeMix FluA/B; and (B) rapid antigen testing using QuickVue (Quidel Corp., San Diego, CA). Table 10 shows that clinically relevant concentrations.

TABLE 10

| Spike-In Organism | Organism Type | Concentration | Clinical Relevancy |
|---|---|---|---|
| Influenza A* (H3N2 and H1N1 subtypes) | (−) ss RNA virus (segmented) | $10^1$ copies | Low |
| | | $10^2$ copies | Medium |
| | | $10^3$ copies | High |
| Influenza B* | (−) ss RNA virus (segmented) | $10^1$ copies | Low |
| | | $10^2$ copies | Medium |
| | | $10^3$ copies | High |

*Whole Influenza virus was grown in MDCK cells

For each influenza A or B concentration (high, medium, low), the qPCR Ct value was lower (optimal) for samples extracted and detected from ATM as compared to Copan UTM. The results achieved are shown in Table 11.

TABLE 11

| Detection | ATM | Copan UTM |
|---|---|---|
| Flu virus = A/California/H1N1 | | |
| High | 29.4 | 30.1 |
| Medium | 30.7 | 32.0 |
| Low | 40.0 | 40.0 |
| Flu virus = A/Texas/H3N2 | | |
| High | 28.6 | 29.6 |
| Medium | 27.4 | 30.9 |
| Low | 34.4 | 40.0 |
| Flu virus = B/Texas/Flu B | | |
| High | 30.7 | 31.8 |
| Medium | 35.1 | 37.2 |
| Low | 39.0 | 39.2 |

Using Rapid Antigen Testing, all mediums were equivalent and detection high and medium concentrations low. Low concentrations ($10^3$ PFU/ml) were below the limit of detection for rapid antigen testing. Tests for ATM and Copan UTM each sample were performed. Results were visualized/verified 15 minutes and one hour after initiation. Table 12 shows the results following this SAS Adeno testing:

TABLE 12

| Detection | Medium | A/California/H1N1 | A/Texas/H3N2 | B/Texas/FluB |
|---|---|---|---|---|
| High | ATM | Pos | Pos | Pos |
| Medium | ATM | Pos | Pos | Pos |
| Low | ATM | Neg | Neg | Neg |
| High | UTM | Pos | Pos | Pos |
| Medium | UTM | Pos | Pos | Pos |
| Low | UTM | Neg | Neg | Neg |

As is clear from the data, A/California/H1N1 medium concentration was detected from virus collected in ATM but not in the sample collected in Copan UTM. ATM facilitated enhanced preservation and detection of viral RNA compared to Copan UTM as assessed by real-time qPCR values. ATM facilitated enhanced detection of viral antigen compared to Copan UTM as assessed QuickVue rapid antigen testing.

Example 6 Extraction-Less PCR with ATM

A clinical specimen ws collected by nasopharyngeal swab and placed in analyte transport medium as disclosed herein (ATM). Aliquots were removed and placed directly in PRIMEMIX® (an all-inclusive qPCR master mix amplification blend; Longhorn Vaccines and Diagnostics, LLC, Bethesda, MD) and analyzed for SARS-CoV-2 RNA on a qPCR instrument. For comparison, identical aliquots were removed and subjected to standard spin-column, total nucleic acid extraction and placed into PRIMEMIX® and analyzed in parallel. There was no difference in detection of viral RNA, or qPCR CT value between extracted and extraction-less specimens. The qPCR (CQ value in triplicate) for each was about 26.3. In addition, extraction-less qPCR detected viral RNA across a 10-fold dynamic range of viral RNA. CQ values were obtained over ten-fold dilutions (genome copies per microliter). At $10^3$, the CQ value obtained was 26.33, at $10^2$, the CQ value obtained was 30.10, and at $10^1$, the CQ value obtained was 38.14.

Collection and transport of specimens in ATM allows rapid qPCR amplification of RNA/DNA without adding proteinase or heating the specimen (each of these steps can be deleterious to RNA/DNA detection). The combination of ATM and PRIMEMIX® (ready-to-use formulation) decreases not only the time required for extraction, but also removes the time required for producing qPCR Master Mix and then adding the primers and probes. This methodology provides safe and rapid qPCR analysis that requires little expertise and training and minimizes the need for ancillary equipment and reagents.

Other embodiments and uses of the invention will be apparent to those skilled in the art from consideration of the specification and practice of the invention disclosed herein. All references cited herein, including all publications, all priority documents, all U.S. and foreign patents and patent applications identified herein, and U.S. Pat. No. 8,084,443 which issued Dec. 27, 2011, U.S. Pat. No. 8,080,645 which issued Dec. 20, 2011, U.S. Pat. No. 8,097,419 which issued Jan. 17, 2012, and International Application No. PCT/US2012/35253 filed Apr. 26, 2012, including the priority documents of each, are specifically and entirely incorporated by reference. The term comprising, wherever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A composition comprising:
   one or more salts;
   one or more sugars which includes a sugar alcohol;
   one or more buffers;
   one or more pH indicators;
   one or more proteins, peptide or amino acids; and
   one or more anti-microbial agents, wherein the composition contains no gelatin and wherein the composition kills or inactivates microorganisms but not viruses.

2. The composition of claim 1, wherein the one or more salts comprises potassium chloride (KCl), calcium chloride ($CaCl_2$), magnesium sulfate ($MgSO_4$), magnesium chloride ($MgCl_2$), potassium phosphate monobasic ($KH_2PO_4$), sodium bicarbonate ($NaHCO_3$), sodium chloride (NaCl), sodium phosphate dibasic ($Na_2HPO_4$), or a combination thereof.

3. The composition of claim 1, wherein the one or more sugars comprise a saccharide monomer, a disaccharide, an oligosaccharide, sucrose, fructose, glucose, dextrose, trehalose, galactose, ribose, deoxyribose, maltose, lactose, or a combination thereof, and/or the sugar alcohol comprises glycerol.

4. The composition of claim 1, wherein the one or more buffers comprise HEPES (4-(2-hydroxyethyl)-1-piperazineethanesulfonic acid), TES (-[[1,3-dihydroxy-2-(hydroxymethyl)propan-2-yl]amino]ethanesulfonic acid), MOPS (3-(N-morpholino)propanesulfonic acid), BES (N,N-bis[2-hydroxyethyl]-2-aminoethanesulfonic acid),
   TIPSO (3-(N,N-Bis[2-hydroxyethyl]amino)-2-hydroxypropanesulfonic acid, N,N-Bis(2-hydroxyethyl)-3-amino-2-hydroxypropanesulfonic acid), MOBS (4-(N-Morpholino)butanesulfonic acid), Tris-HCl, citrate, MES, Bis-Tris, Bicine, Tricine, ADA (2,2',2''-Nitrilotriacetic acid), ACES (N-2-aminoethanesulfonic acid), PIPES (piperazine-N,N'-bis), bicarbonate, phosphate, or a combination thereof.

5. The composition of claim 1, wherein the one or more pH indicators comprise phenol red (3H-2,1-benzoxathiole 1,1-dioxide), neutral red 3-amino-(7-dimethylamino-2-methylphenazine hydrochloride), or a combination thereof.

6. The composition of claim 1, wherein the one or more proteins comprise bovine serum albumin (BSA; acetylated or non-acetylated), L-glutamic acid, L-glutamine, alanyl-1-glutamine, glycyl-1-glutamine, L-cysteine, or a combination thereof.

7. The composition of claim 1, wherein the one or more anti-microbial agents comprise colistin, amphotericin B, vancomycin, streptomycin, polymyxin B, or a combination thereof.

8. The composition of claim 1, which has a pH of from about pH 6.5 to a pH of about 7.5.

9. The composition of claim 1, further comprising a biological sample.

10. The composition of claim 9, wherein the biological sample is suspected of containing mammalian tissue, a viral organism, a bacterial organism, a parasitic or a fungal organism.

11. A method of transporting a biological sample containing microorganisms without refrigeration comprising:
    collecting the biological sample;
    combining the biological sample with the composition of claim 1, wherein substantially all nucleic acid sequences of the microorganisms remain detectable subsequent to combining.

12. The method of claim 11, wherein ambient temperature comprises temperatures from about 15° C. to about 30° C.

13. The method of claim 11, wherein the composition combined with the biological sample are maintained at ambient temperature or greater for at least 3-7 days.

14. The composition of claim 1, wherein the composition sterilizes the biological sample.

15. The composition of claim 9, which substantially lowers the count of microorganisms of the biological sample.

16. A composition consisting essentially of:
    one or more salts;
    one or more sugars which includes a sugar alcohol;
    one or more buffers;
    one or more pH indicators;

one or more proteins, peptide or amino acids; and
one or more anti-microbioal agents, wherein the composition contains no gelatin.

17. The composition of claim 16, wherein the antimicrobial agents comprise one or more antibacterial agents.

18. The composition of claim 16, wherein the antimicrobial agents comprise one or more antiparasitic agents.

19. The composition of claim 16, wherein the antimicrobial agents comprise one or more antifungal agents.

20. The composition of claim 16, wherein the composition preserves viruses.

21. The composition of claim 1, wherein the one or more salts are at an amount of from about 0.1% to about 1%, the one or more sugars are at an amount of from about 2% to about 10%, the one or more buffers are at an amount of from about 0.2% to about 1%, the one or more proteins, peptide or amino acids are at an amount of from about 0.2% to about 1%, and the one or more anti-microbial agents are at an amount of about 0.001% to about 0.000001%.

22. The composition of claim 16, wherein the one or more salts are at an amount of from about 0.1% to about 1%, the one or more sugars are at an amount of from about 2% to about 10%, the one or more buffers are at an amount of from about 0.2% to about 1%, the one or more proteins, peptide or amino acids are at an amount of from about 0.2% to about 1%, and the one or more anti-microbial agents are at an amount of about 0.001% to about 0.000001%.

* * * * *